US00PP15051P3

(12) United States Plant Patent
Martins

(10) Patent No.: US PP15,051 P2
(45) Date of Patent: Jul. 27, 2004

(54) CACTACEAE PLANT NAMED 'PRANCER'

(50) Latin Name: *Schlumbergera truncata*
Varietal Denomination: Prancer

(75) Inventor: Mario L. Martins, Half Moon Bay, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 10/295,386

(22) Filed: Nov. 14, 2002

(65) Prior Publication Data

US 2004/0098778 P1 May 20, 2004

(51) Int. Cl.[7] ..... A01H 5/00
(52) U.S. Cl. ..... Plt./372

(58) Field of Search ..... Plt./372

*Primary Examiner*—Anne Marie Grunberg
*Assistant Examiner*—S B McCormick-Ewoldt
(74) *Attorney, Agent, or Firm*—Charles R. Cypher; James R. Cypher

(57) ABSTRACT

A plant variety of the Cactaceae family resulting from a controlled crossing of *Schlumbergera truncata* 'Camillia' and *Schlumbergera truncata* 'Rudolph II' (U.S. Plant Pat. No. 10,487) called 'Prancer'. 'Prancer' has a bi-colored bloom, due to the tube forming tepals having red-purple coloring at their margins and white central and basal surfaces. 'Prancer' has a strong resistance to bud abscission, a strong propensity for buds to mature and flower, considerable resistance to fungal diseases, an erect growth habit, and an ability to grow well in relatively cold temperatures. 'Prancer' also possesses a fast growth rate, and a strong propensity to branch with minimal pruning.

4 Drawing Sheets

Latin name of the genus and species of the plant claimed: The new plant is a variety of *Schlumbergera truncata*.

Variety denomination: The new plant has been given the varietal designation 'Prancer'.

BACKGROUND OF THE INVENTION

The present invention relates to a new and distinct variety of the Cactaceae family. The new variety is named *Schlumbergera truncata* 'Prancer'. The inventor is Mario Luciano Martins of Half Moon Bay, Calif., a citizen of the United States.

Many varieties of *Schlumbergera truncata* tend to bloom in the months of November and December in the Northern Hemisphere. Because of their blooming time, there is a large market for these varieties during the Thanksgiving and Christmas seasons as a decorative plant. In fact, one common name for these plants is Christmas Cactus.

There are many commercially developed varieties of Christmas Cactus. Patented varieties include: 'Lavender Doll' (Cobia, U.S. Plant Pat. No. 3,690); 'Christmas Charm' (Cobia et al., U.S. Plant Pat. No. 4,196); 'Rudolph' (Higaki, U.S. Plant Pat. No. 6,234); 'Dasher' (Higaki, U.S. Plant Pat. No. 7,367); and 'Rudolph II' (Martens, U.S. Plant Pat. No. 10,487).

For many varieties of the species, bud abscission is a problem: a large portion of the initial buds that form on the plant fall off before they reach full maturity. Furthermore, many cultivars possess the further undesirable characteristic that many of the buds that do set on the plant fail to mature and bloom. Preferred cultivars resist bud abscission, as well as produce buds that have a propensity to mature.

The present variety resists bud abscission, as well as produces buds that have a propensity to mature. The present variety sets many buds per phylloclade (often 2 to 3), many of which reach full maturity and bloom (generally 1 to 2). This present variety is also outstanding for its propensity to grow tall and upright, thus giving it a dense appearance.

Commercially preferred varieties also possess: a fast growth habit, and a resistance to fungal diseases and nutrient deficiencies. The variety of the present invention possesses all the above mentioned characteristics.

The flowers of the present variety present a bi-colored appearance. The color of the pigmentation in the sepals of the new variety falls in the Red-Purple Group, according to The Royal Horticultural Society of London's Colour Chart.

This new variety of *Schlumbergera truncata* was the result of a controlled cross by the inventor between *Schlumbergera truncata* 'Camillia' (an unpatented commercial variety) and *Schlumbergera truncata* 'Rudolph II' (U.S. Plant Pat. No. 10,487). The cross was carried out at a nursery in the city of Half Moon Bay. Half Moon Bay is located in the country of San Mateo, in the state of California.

The inventor first identified the new variety by its flower color and its upright growth habit.

Comparison Chart of Flower Pigmentation Color

| | 'Prancer' New Variety | 'Rudolph II' (Parent) U.S. Plant Patent 10,487 | 'Camillia' (Parent) Unpatented commercial var. | 'Dark Maria' Unpatented commercial var. | 'Maria' Unpatented commercial var. |
|---|---|---|---|---|---|
| Mature Flower Pigmentation Color in Tepals | R.H.S. 74 A | R.H.S. 47 A | R.H.S. 74 B | R.H.S. 46 A | R.H.S. 45 C |

The flowers of the plant can be characterized as bicolor flowers. The pigmented portion of the blades at their margins of the sepaloid tepals, the tube laminating tepals, and the tube forming tapels is R.H.S. 74 A (red-purple group), while in the remaining portions of the flower, the pigmentation quickly fades, providing a white appearance, especially in the tube laminating and tube forming tepals.

The new variety's improved resistance to bud abscission results in the setting of 1 to 3 buds per phylloclade.

Because the buds of the new variety have a greater propensity to mature, when grown under the proper conditions, at least one bud and often 2 buds that do set on a phylloclade will mature and bloom.

The distinguishing characteristics of the new variety are retained by asexually reproduced, successive generations.

In addition, the new variety also possesses the additional commercially desirable characteristics of:

1. a fast growth rate;
2. a strong propensity to branch with minimal pruning, resulting in a dense appearance;
3. erect stems, resulting in an upright appearance;
4. a considerable resistance to fungal diseases such as Potritus; and
5. an ability to grow in colder temperatures.

The new variety generally forms one to three branches from the propagated cutting.

The inventor has asexually reproduced the new variety at a commercial nursery in Half Moon Bay, Calif. through three successive generations by cuttings, and has found that the combination of characteristics as herein disclosed remain firmly fixed.

BRIEF DESCRIPTION OF THE DRAWING

The accompanying drawings serve, by color photographic means, to illustrate the new plant variety. The colors are represented as truly as possible using conventional photographic procedures.

DETAILED DESCRIPTION OF THE NEW VARIETY

Figure 1:
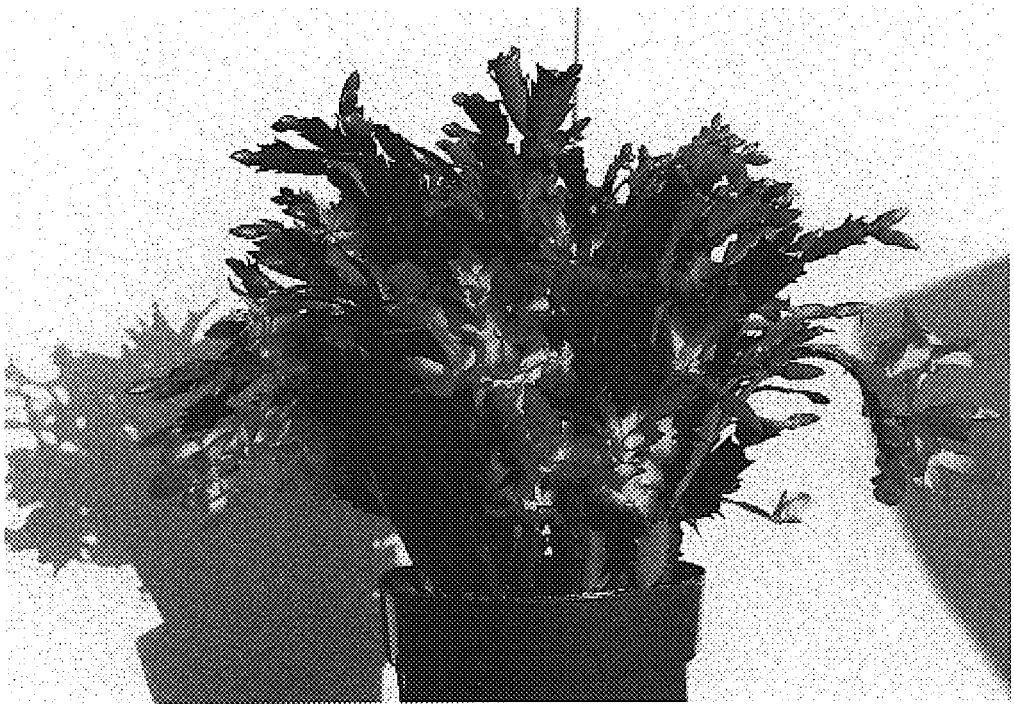
FIG. 1 is a color photograph of a number of plants grown from a number of cuttings in one pot of the new variety illustrating the overall appearance and form of the plant, and the abundance of blooms.
Figure 2:
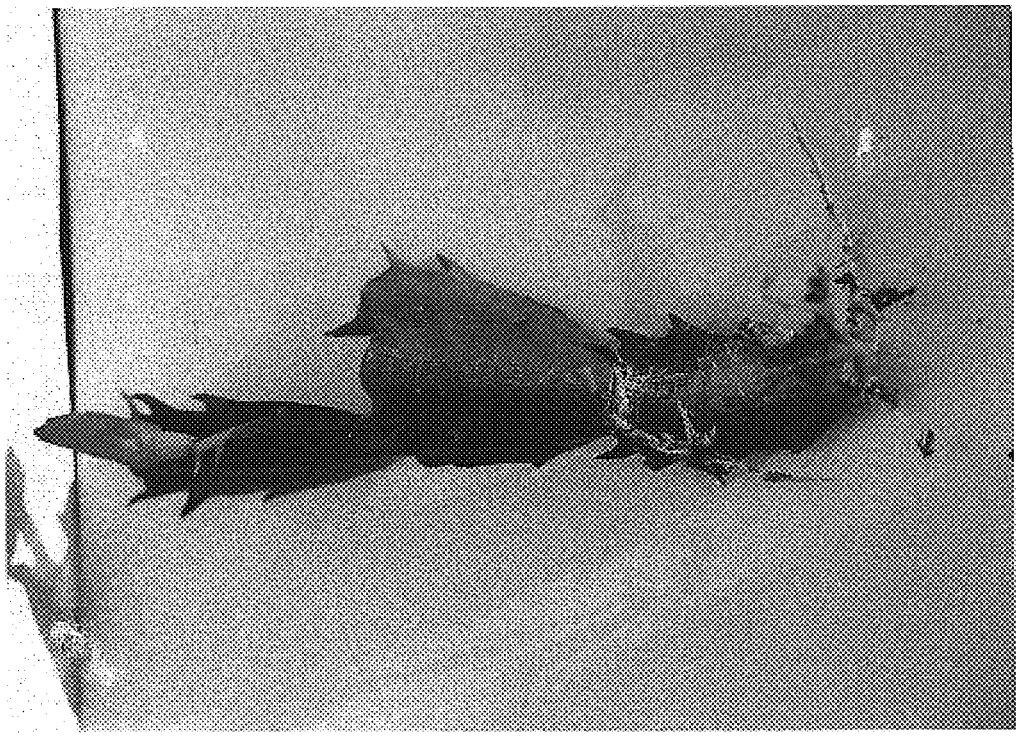
FIG. 2 is a color photograph of a single plant removed from its soil, and with many of its branches removed, that was propagated from a single phylloclade cutting.
Figure 3:
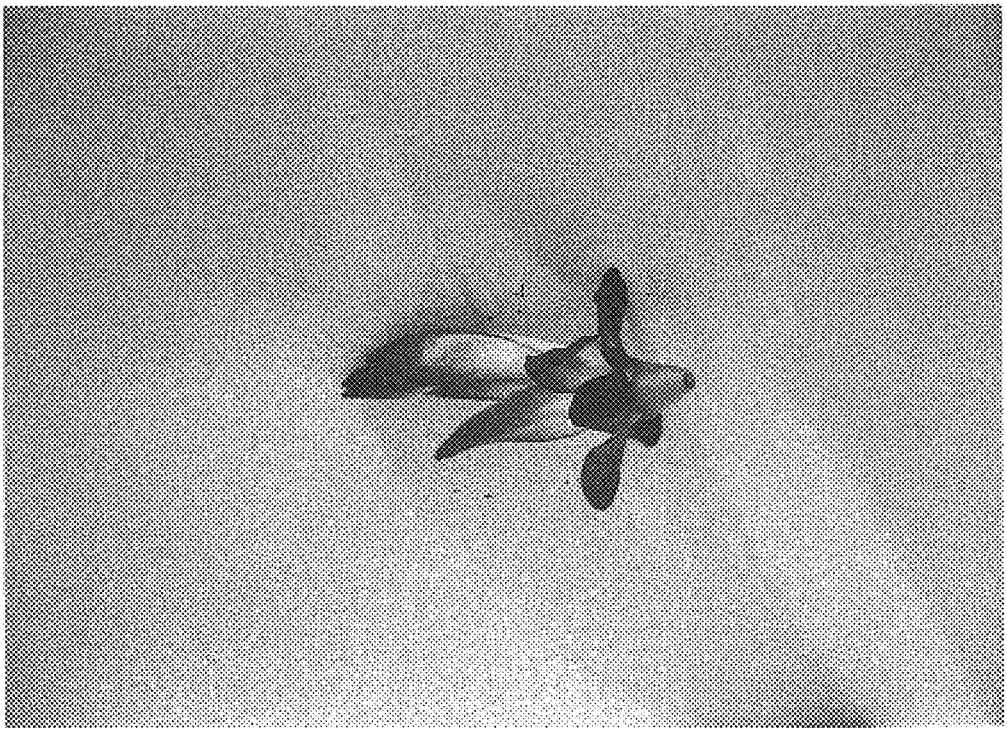
FIG. 3 is a color photograph showing a side view of a partially opened bloom of the new variety.
Figure 4:
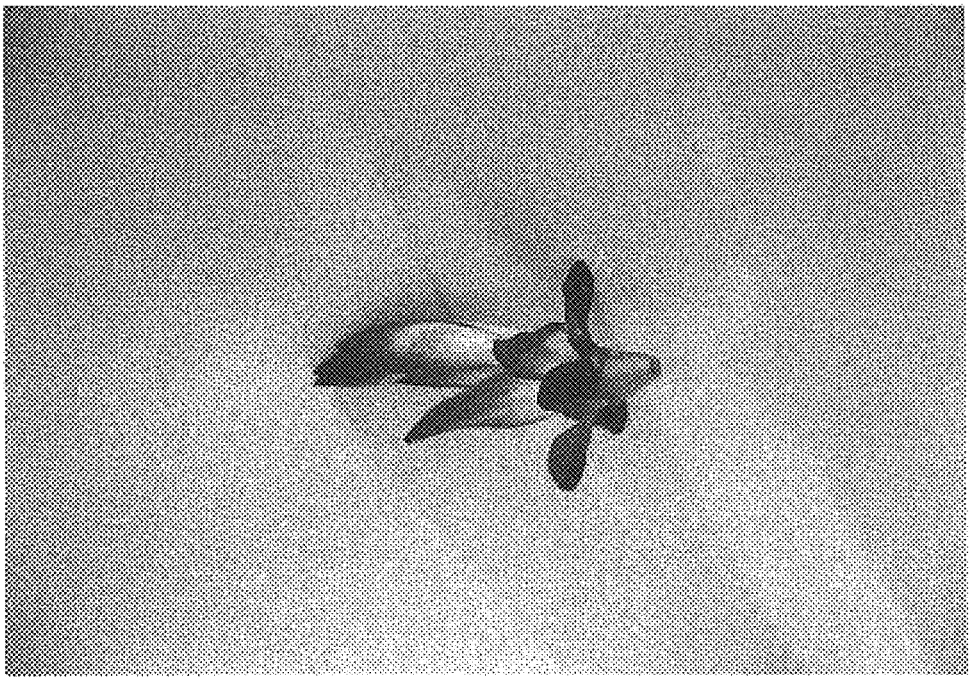
FIG. 4 is a color photograph a partially opened bloom of the new variety.
Figure 5:
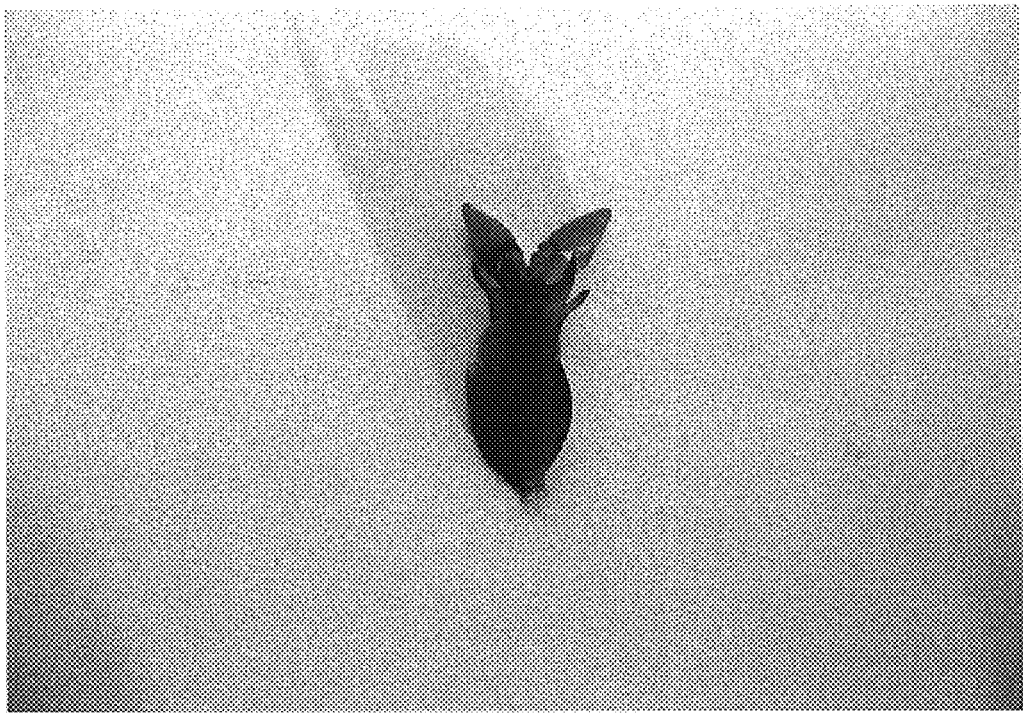
FIG. 5 is a color photograph of a phylloclade having two buds growing from its apex.
Figure 6:
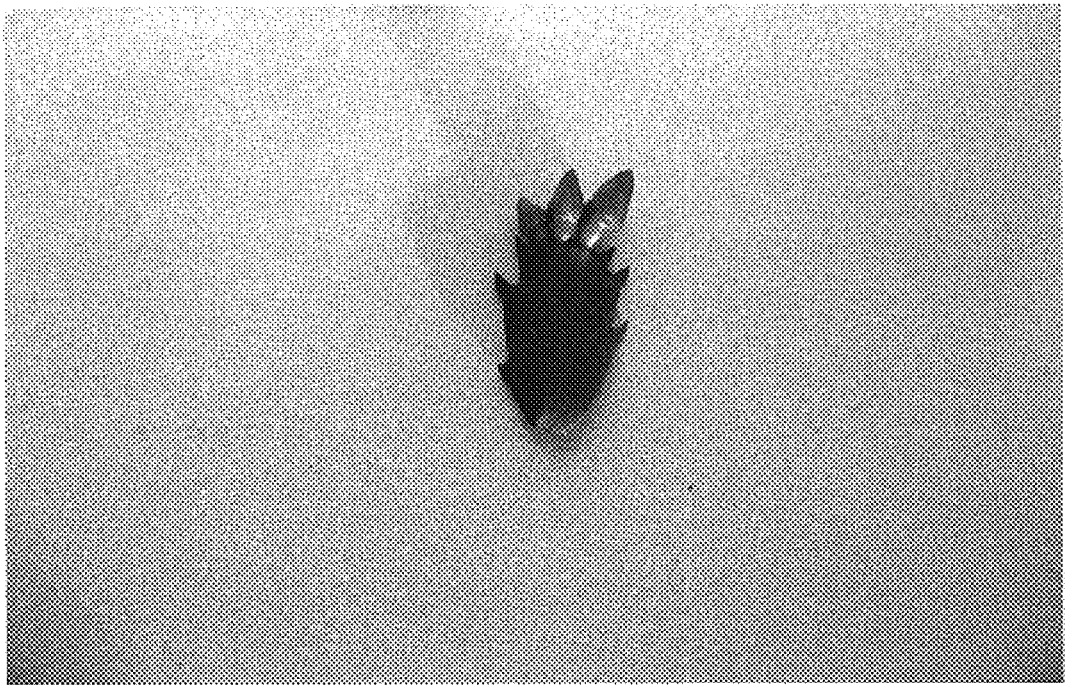
FIG. 6 is a color photograph of a phylloclade having three buds growing from its apex.
Figure 7:
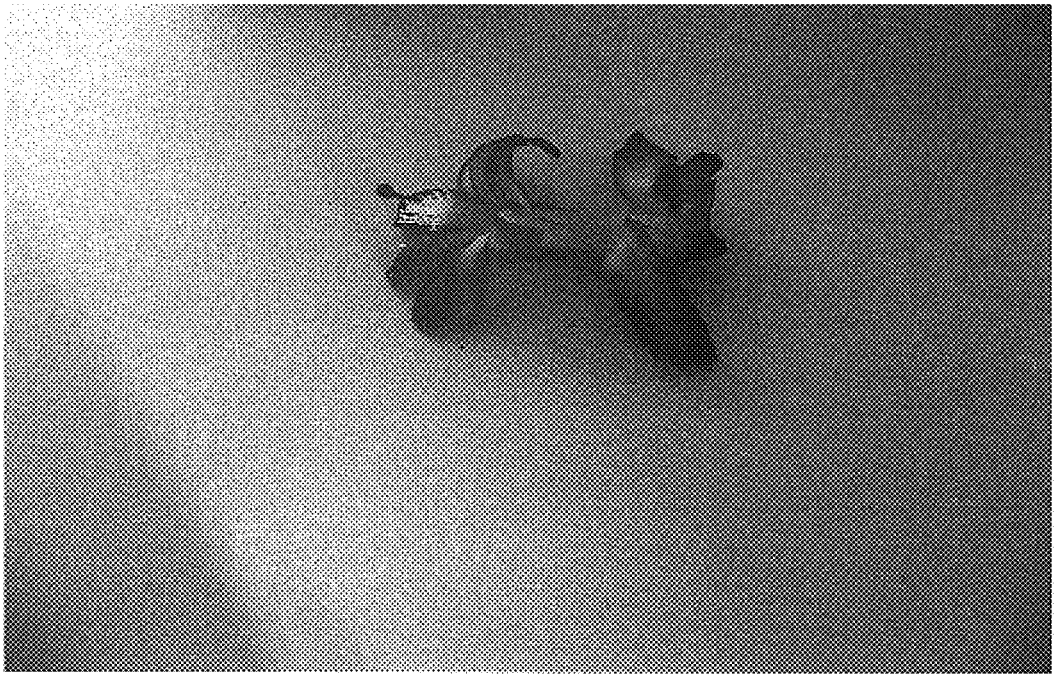
FIG. 7 is a color photograph of fully opened flower of the new variety.
Figure 8:
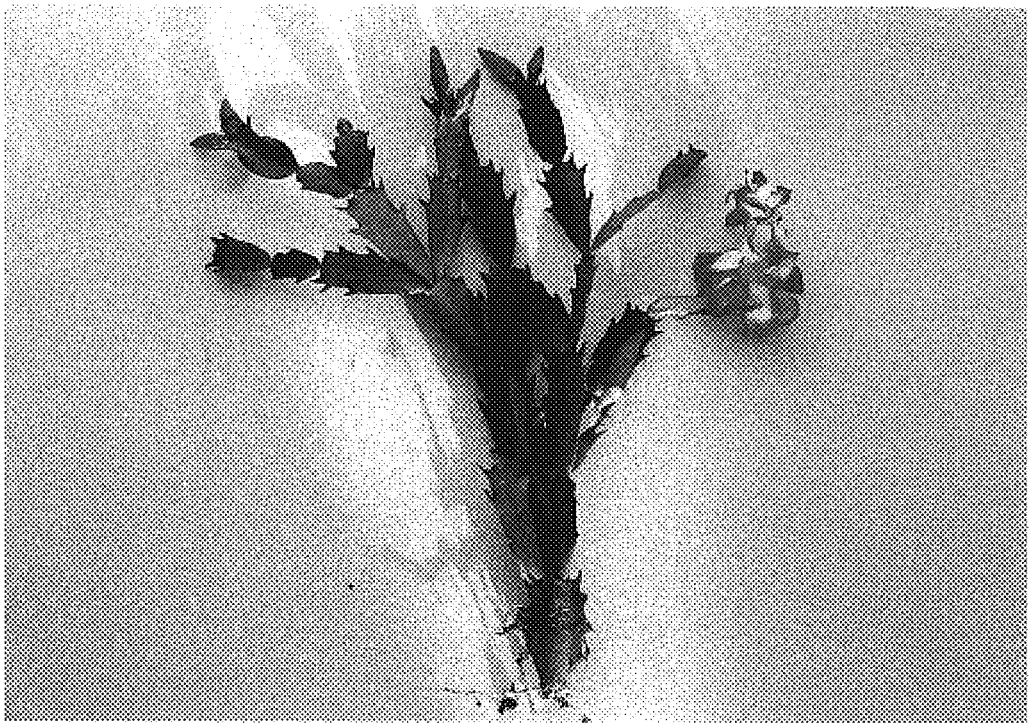
FIG. 8 is a color photograph of a single plant removed from its soil that grew from a single phylloclade cutting.

The following is a detailed description of the new variety. The new variety has not been observed under all possible environmental conditions. Color designation and other values stated may deviate slightly from the stated values from flowering to flowering, but the deviations will be within the range expected from varying environmental, seasonal and cultural conditions. Color designations were made according to The R.H.S. Colour Chart published by The Royal Horticultural Society of London, England.

The plants observed were grown in 6 inch pots. The tops of the plants observed were approximately 22 to 28 centimeters above the soil level. The following description is based on observations of optimally fertilized plants grown at a nursery in Half Moon Bay, Calif. The observed plants were grown from phylloclade cuttings placed in the soil of the pots with multiple phylloclades placed in each pot. The phylloclades set roots in approximately 1 to 2 months time. The observed plants were approximate 12 months old. Temperatures in Half Moon Bay on average range from 55 to 65 degrees Fahrenheit in the summer months, and from 45 to 55 degrees Fahrenheit in the winter months.

DETAILED PLANT DESCRIPTION

Name: *Schlumbergera truncata* 'Prancer'.

Parentage: Controlled cross between *Schlumbergera truncata* 'Camillia' (an unpatented commercial variety) and *Schlumbergera truncata* 'Rudolph II' (U.S. Plant Pat. No. 10,487).

Classification:

*Family.*—Cactaceae.

*Tribe.*—Cereus (Cacteae).

*Genus.*—Schlumbergera.

*Species.*—*Schlumbergera truncata* (Haw.) Moran [*Epiphyllum truncatum* Haw.; *Zygocactus truncatus* (Haw.) K. Schum.]. Bailey and Bailey and the staff of the Bailey Hortorium, *Hortus Third* (1976).

*Commercial.*—Thanksgiving Cactus, Christmas Cactus.

Form: Terrestrial, shade-loving, succulent, leafless plant with jointed and branched stems. Plant grown from a single phylloclade cutting placed in soil is as wide as 10 inches.

Stems:

*General.*—Irregular with usually mono-chotomous to di-chotomous, and sometime tri-chotomous, branching of upright, adventitiously rootable, flattened phylloclades that have a prominent midrib (especially in phylloclades at the base of mature plants) and prominently toothed lateral wings.

*Phylloclades.*—General: The phylloclades are obovate to oblong, elongated and flattened (particularly when young) and have a transversely elongated, areole bearing, truncated apex. From the transversely elongated apex, the wing margins generally run straight or taper slightly to the basal portions (or occasionally they flare outwardly somewhat), where they then taper and merge through a pointed, basal juncture with the phylloclade therebelow. The margins are also toothed and an axillary aerole is associated with each tooth. Size: Length — Mature phylloclades that are over a year old are usually between 45 mm and 60 mm. Width — Mature phylloclades that are over a year old are usually 16 mm to 26 mm. Thickness — Basal phylloclades with up to three levels of phylloclades above them can be as thick as 1 cm at the midrib. Young phylloclades are as thick as 3 to 4 mm at the center, and tapering to 1 mm near the edges. Color: Portions of the phylloclades exposed to the light are predominately R.H.S. 137 B & C (yellow-green group), while shaded phylloclade portions are predominantly R.H.S. 144 A (yellow-green group). Midrib: General — Extends longitudinally of phylloclade and continuously through joints with laterally tapering cortex at wing insertions. Pith surrounds the vascular bundles that branch and provide lateral extensions of the vascular system to marginal teeth. Texture — Smooth, waxy epidermis with wax in small embedded scales and becoming corky in basal stem areas with age. Wings: General shape — Generally flattened from midrib cortex to tooth insertions with slight thinning taper toward margins. Margins — Toothed (modified leaves). Texture — Succulent to leathery with smooth, waxy epidermis having wax arranged in small embedded scales and becoming corky in basal plant areas with age. Teeth: General shape — Generally flattened and tapering along margins from wing insertion to an apex having a hyaline, pointed spine with nonpredicatable bending. Adaxial margin shape: Generally concave, so that teeth project generally distally of the phylloclade base in an alternate arrangement, but also with both straight and convex adaxial margin tendencies. Abaxial margin shape: Irregular with tendencies toward straight to convex. Tooth Margins: Entire. Texture — Succulent to leathery with a smooth waxy epidermis having wax in small embedded scales and becoming corky in basal plant areas with age. Number — Usually 3 to 4 on each side. Size — Teeth of mature phylloclades are 1 mm thick at insertion point with wings. Areole to apex dimension (adaxial margin side): usually 5 to 8 mm in length. Areoles: Terminal areole — Large, compound, elongated, oval-shaped with several acicular bristles, copious multi-cellular hairs, and several buds that may mature into either new phylloclades or flowers. The opposite ends of the areole are located adjacent to subsidiary aeroles which are in turn located at the axils of the uppermost teeth located at the distal end of the of phylloclade. Axially areoles — Acicular bristles without glochidia but having copious, short, brownish to colorless, multicellular hairs. Areoles are commonly found in the basal portion of the phylloclade in association with a vestigial tooth that is less than 1 mm in length. (Vestigial teeth not considered in teeth number or length of teeth.)

Buds: Unarmored and ovid, generally R.H.S. 67 A (red-purple group). Once buds form they grow until maturity or they fall off the plant before flowering.

Flowers:

*General.*—Sessile, zygomorphic, usually solitary or in pairs, terminal, perfect, and epigynous with double hypanthium and tepals (undifferentiated whorled sepals and petals) having a spiral emergence as a perianth provided with a sepaloid series of free tepals, a tube laminating series of tepals, and a tube forming series of united tepals.

*Sepaloid series of tepals.*—General: Free tepals inserted on top of the ovary. Shape: Deltoid in outer members of the whorl and grading inwardly on the whorl to tepals which are ovate and less frequently elliptical. Tips are broadly acuminate with some acute tendencies, and margins are entire with sparse irregular teeth appearing mainly in the apex areas. Texture: Succulent and glabrous outer whorl members and grading inwardly in the whorl to silken blades with fleshy basal areas. Number: Usually 8. Size (at full bloom): Base-tip dimension — 9 mm to 17 mm. Width dimension — 7 mm to 10 mm. Color: The sepaloid series of tapals are predominantly R.H.S. 74 A (red-purple group) with only small basal portions lacking pigment.

*Tube laminating series of tepals.*—General: Tepals inserted on ovary and basally united below the throat as outer laminations on the perianth tube and with progressively greater amounts of basal fusion inwardly in the whorl. Shape: Grading inwardly in the whorl with progressively longer base-tip dimensions and with blade areas changing inwardly from ovate to broadly elliptical and with acute tips. Entire margins with sparse irregular teeth mainly in apex areas. Texture: Succulent, slightly fleshly basal areas with silken blades. Number: 6. Size (at full bloom): Base-tip dimension — 50 mm to 60 mm. Width dimension — 14 and 15 mm. Color: The margins and distal ends of the tube laminating series of sepals are R.H.S. 74 A (red-purple group); however, the central portions of these tepals lack pigment.

*Tube forming series of tepals.*—General: Tepals basally united to form a hollow perianth tube that is inserted on ovary and equipped with a irregular carina (keel) at the throat. Shape: Perianth tube — Elongated and ellipsoidal to oval in cross-section. Blades — Generally elliptic to broadly elliptic with ovate tendencies and with acuminate tips. Entire margins with sparse, irregular teeth mainly in apex area. Carina (keel) — Transcending and irregular. Texture: Perianth tube — Thick, succulent, and slightly ribbed. Blades — Translucent and silken. Carina (keel) — Fleshy. Blade number: 5. Size (at full bloom): Base-tip dimension — 50 mm to 60 mm. Perianth tube — Base to throat length is 35 mm. Color (at full bloom): Perianth tube — white. Blades — Margins and much of the blades at maturity are R.H.S. 74 A (red-purple group). Orientation at full bloom: reflexed.

*Androecium* (*stamens*).—General: Numerous exserted and diadelphous stamens with one group having filaments basally fused to the perianth tube and the other group having filaments basally united to form a nectary housing. Filament: General — Translucent and glabrous with anther connective. Shape — Long, slender and gradually tapering from base to anther connective. Texture — Glabrous and silken. Color — Translucent white. Size (at full bloom) — Length: 40 mm to 60 mm. Anters: Shape — Rod shaped. Size — 1 mm long. Texture — Course or grainy. Color (pollen color) — R.H.S. 1D (yellow group).

*Gynoecium* (*pistil*).—General: Compound, parietal placentation with united style surrounded by an annular diffuse nectary at its insertion. Style: General — Stout and inserted in ovary. Shape — Elongated. Texture — Fleshy and glabrous. Color — R.H.S. 74 A (red-purple group). Size (at full bloom) — 40 to 60 mm long. Stigma: General — Exserted and erect with usually 6 to 7 inner marginally adhering lobes. Shape — Elongated and tapering toward lobe tips and having relatively blunt apices. Texture — Fleshy and smooth with short glutinous hairs. Color — R.H.S. 74 A (red-purple group). Size — 3 mm long. Ovary: General — Thin epidermis and distally located concavity, and with a single cavity usually having 6 to 7 carpels with numerous ovules. Shape — Terete to ovoid and generally broadening from insertion to floral end. Texture — Succulent and glabrous with thin outer epidermis.

*Fruit.*—Generally flowers wither and become desiccated along with the ovary and together they fall of the plant. As the ovaries fall of the plant, the plant does not produce a fruit or seeds.

Fragrance: No fragrance.

I claim:

1. A new and distinct Cactaceae plant as herein described and illustrated.

* * * * *